US 011497444B2

(12) United States Patent
Tamaki et al.

(10) Patent No.: US 11,497,444 B2
(45) Date of Patent: Nov. 15, 2022

(54) BIOLOGICAL INFORMATION MEASUREMENT DEVICE

(71) Applicant: H2L Inc., Tokyo (JP)

(72) Inventors: Emi Tamaki, Tokyo (JP); Kenichiro Iwasaki, Tokyo (JP)

(73) Assignee: H2L Inc., Tokyo (JP)

( * ) Notice: Subject to any disclaimer, the term of this patent is extended or adjusted under 35 U.S.C. 154(b) by 315 days.

(21) Appl. No.: 16/645,287

(22) PCT Filed: Jun. 27, 2018

(86) PCT No.: PCT/JP2018/024438
§ 371 (c)(1),
(2) Date: Mar. 6, 2020

(87) PCT Pub. No.: WO2019/058688
PCT Pub. Date: Mar. 28, 2019

(65) Prior Publication Data
US 2021/0022674 A1  Jan. 28, 2021

(30) Foreign Application Priority Data
Sep. 20, 2017 (JP) .............................. JP2017-180305

(51) Int. Cl.
*A61B 5/00* (2006.01)
*A61B 5/107* (2006.01)
*A61B 5/11* (2006.01)

(52) U.S. Cl.
CPC ............ *A61B 5/681* (2013.01); *A61B 5/1079* (2013.01); *A61B 5/1107* (2013.01); *A61B 5/4519* (2013.01)

(58) Field of Classification Search
CPC .................................................... A61B 5/861
See application file for complete search history.

(56) References Cited

U.S. PATENT DOCUMENTS

2010/0130841 A1* 5/2010 Ozawa .................. A61B 5/681
600/323
2015/0105221 A1 4/2015 Roush et al.
(Continued)

FOREIGN PATENT DOCUMENTS

JP  2013-150847 A  8/2013
JP  2015-112488 A  6/2015
(Continued)

OTHER PUBLICATIONS

International Search Report (ISR) dated Aug. 7, 2018 filed in PCT/JP2018/024438.

*Primary Examiner* — Brian T Gedeon
(74) *Attorney, Agent, or Firm* — Rankin, Hill & Clark LLP

(57) ABSTRACT

Provided is a biological information measuring instrument which can be easily and reliably worn on an appropriate position of an arm by a user. The biological information measuring instrument includes: a belt portion that is worn on a user's arm in a circumferential direction of the arm and disposed with a sensor for detecting a displacement of an arm muscle; and a case portion that is attached to a predetermined portion of the belt portion and houses a circuit component that processes a signal of the displacement detected by the sensor. The case portion has a shape of protruding from the belt portion in a longitudinal direction of the arm when the belt portion is worn on the arm, and amounts D1 and D2 of protrusions protruding in the longitudinal direction are different between one protrusion and the other protrusion.

4 Claims, 8 Drawing Sheets

(56) References Cited

U.S. PATENT DOCUMENTS

| | | |
|---|---|---|
| 2015/0160048 A1 | 6/2015 | Schuessler |
| 2016/0022181 A1 | 1/2016 | Valsan et al. |
| 2016/0091980 A1* | 3/2016 | Baran .................. A61B 5/6824 345/156 |
| 2019/0022373 A1 | 1/2019 | Tamaki et al. |

FOREIGN PATENT DOCUMENTS

| | | |
|---|---|---|
| JP | 2016-30214 A | 3/2016 |
| JP | 2016-533256 A | 10/2016 |
| JP | 2017-131362 A | 8/2017 |

* cited by examiner

BIOLOGICAL INFORMATION MEASUREMENT DEVICE

TECHNICAL FIELD

The present invention relates to a biological information measuring instrument suitable for use in a controller for operating a game, a robot, a computer, or the like.

BACKGROUND ART

In recent years, with progress of virtual reality technology and spread of head-mounted displays, video games that allow various experiences in a virtual space presented by video have been developed.

When such a video game is operated by a user, the user feels more realistic sensation in operation by movement of the user's hand or finger than in operation using a controller with conventional buttons and keys. For example, it is known to detect the movement of the user's hand from the video taken using a video camera and reflect the detected movement of the hand in the video game.

However, when detecting a user's movement using the video camera, it is impossible to detect finger movement or the like that cannot be seen from the video camera in principle, because it is only possible to perform an operation based on the user's movement that can be taken by the video camera.

In order to solve this problem, the present applicant has proposed a technique for detecting the movement of the finger with a measuring instrument previously worn on the user's arm (see PATENT LITERATURE 1).

The technique described in PATENT LITERATURE 1 detects the movement of the user's finger by detecting a displacement of muscle that moves the finger by an optical distance sensor disposed in the measuring instrument worn on the user's arm. In the measuring instrument described in PATENT LITERATURE 1, the optical distance sensor for detecting the displacement of the muscle is disposed, and an electrode for stimulating the muscle is disposed in addition to the optical distance sensor, so that it has bidirectionality to control the movement of the finger while detecting the movement of the user's finger.

CITATION LIST

Patent Literature

PATENT LITERATURE 1: JP-A-2017-131362

SUMMARY OF THE INVENTION

Problems to be Solved by the Invention

When performing the game using the video such as the virtual space as described above, the measuring instrument worn on the user's arm is preferably made as small and light as possible so as not to give the user a sense of discomfort while performing the game. Therefore, it is conceivable to omit the electrode for stimulating the muscle from the measuring instrument described in PATENT LITERATURE 1 and to make a small measuring instrument in which only the optical distance sensor is disposed.

However, when the measuring instrument is simply made small, there is a problem that a wearing position of the measuring instrument is not always appropriate. That is, the sensor for detecting the displacement of the muscle has a limited detection position appropriate for detecting the displacement of the muscle, and the measuring instrument is required to be worn at a predetermined position of the arm. Specifically, the optical distance sensor is preferably placed on the arm (a forearm) at a position several centimeters away from a wrist; however, when the measuring instrument is small, it is not always worn at such a position. For example, when the measuring instrument is worn around the wrist, there may be a case where the displacement of the muscle cannot be detected. In such a case, it will be in a state of use in which an original measuring ability of the measuring instrument is not utilized.

An object of the present invention is to provide the biometric information measuring instrument which can be easily and reliably worn on an appropriate position of the arm by the user.

Solution to the Problems

A biological information measuring instrument of the present invention includes: a belt portion that is worn on a user's arm in a circumferential direction of the arm and disposed with a sensor for detecting a displacement of an arm muscle; and a case portion that is attached to a predetermined portion of the belt portion and houses a circuit component that processes a signal of the displacement detected by the sensor.

The case portion has a shape of protruding from the belt portion in a longitudinal direction of the arm when the belt portion is worn on the arm, and amounts of protrusions protruding in the longitudinal direction are different between one protrusion and the other protrusion.

Effects of the Invention

According to the present invention, since the case portion has a shape protruding from the belt portion, when the belt portion is worn on the user's arm, the belt portion can be worn on the arm away from the wrist by a certain distance. For example, the belt portion can be automatically worn on the appropriate position of the arm by attaching a guide mark or the like so that the belt portion is worn on the arm with the protrusion more largely protruding from the belt portion being directed to the wrist. Therefore, since the sensor disposed on the belt portion can satisfactorily detect the displacement of the muscle accompanying the movement of the finger, it is possible to satisfactorily measure biological information.

DESCRIPTION OF THE EMBODIMENTS

Hereinafter, a biological information measuring instrument of an embodiment of the present invention (hereinafter, referred to as a "present embodiment") will be described with reference to the accompanying drawings.

1. Structure of Biological Information Measuring Instrument

Figure 1:
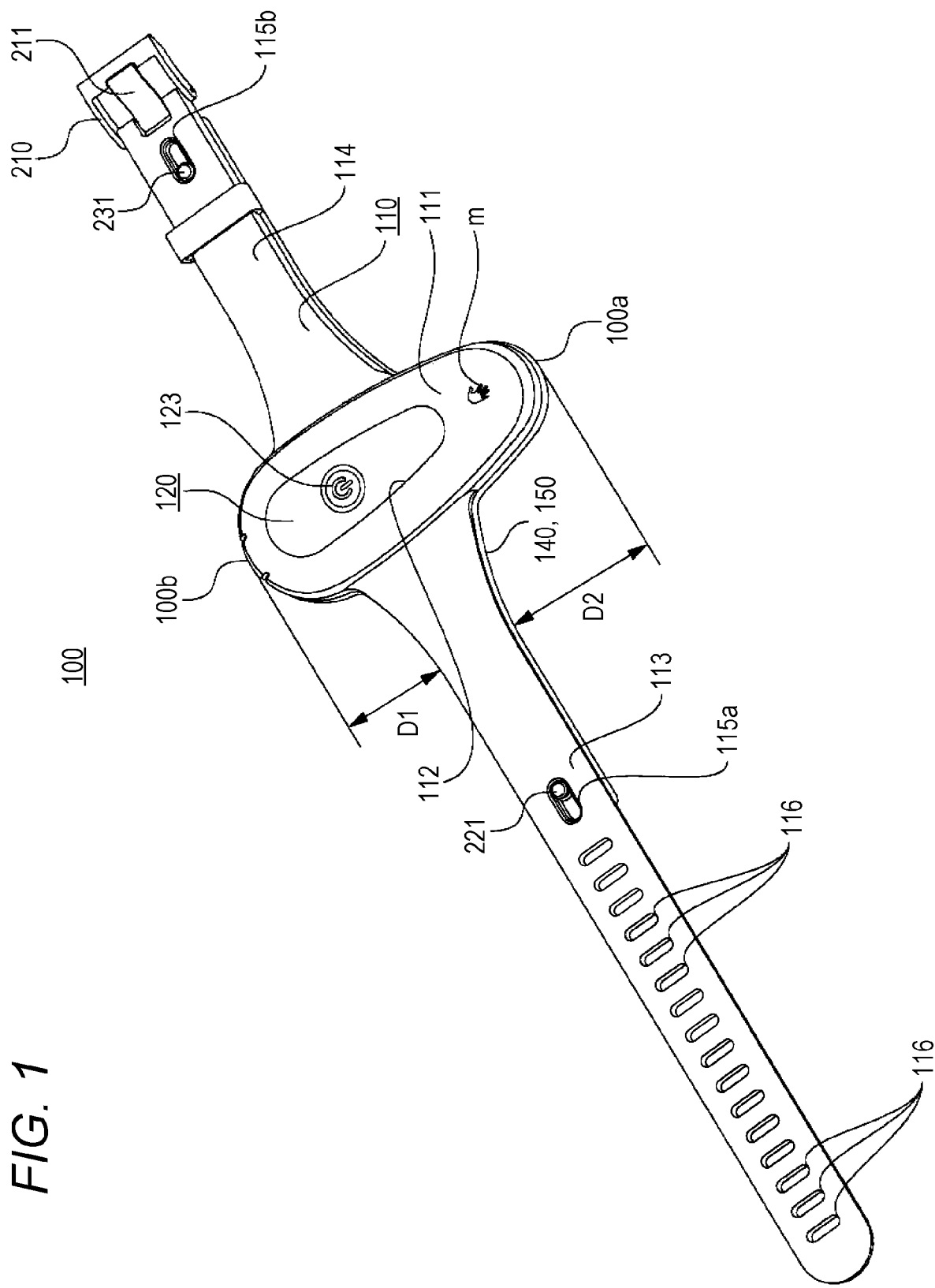
FIG. 1 is a perspective view of a front surface side of a biological information measuring instrument according to an embodiment of the present invention.
Figure 2:
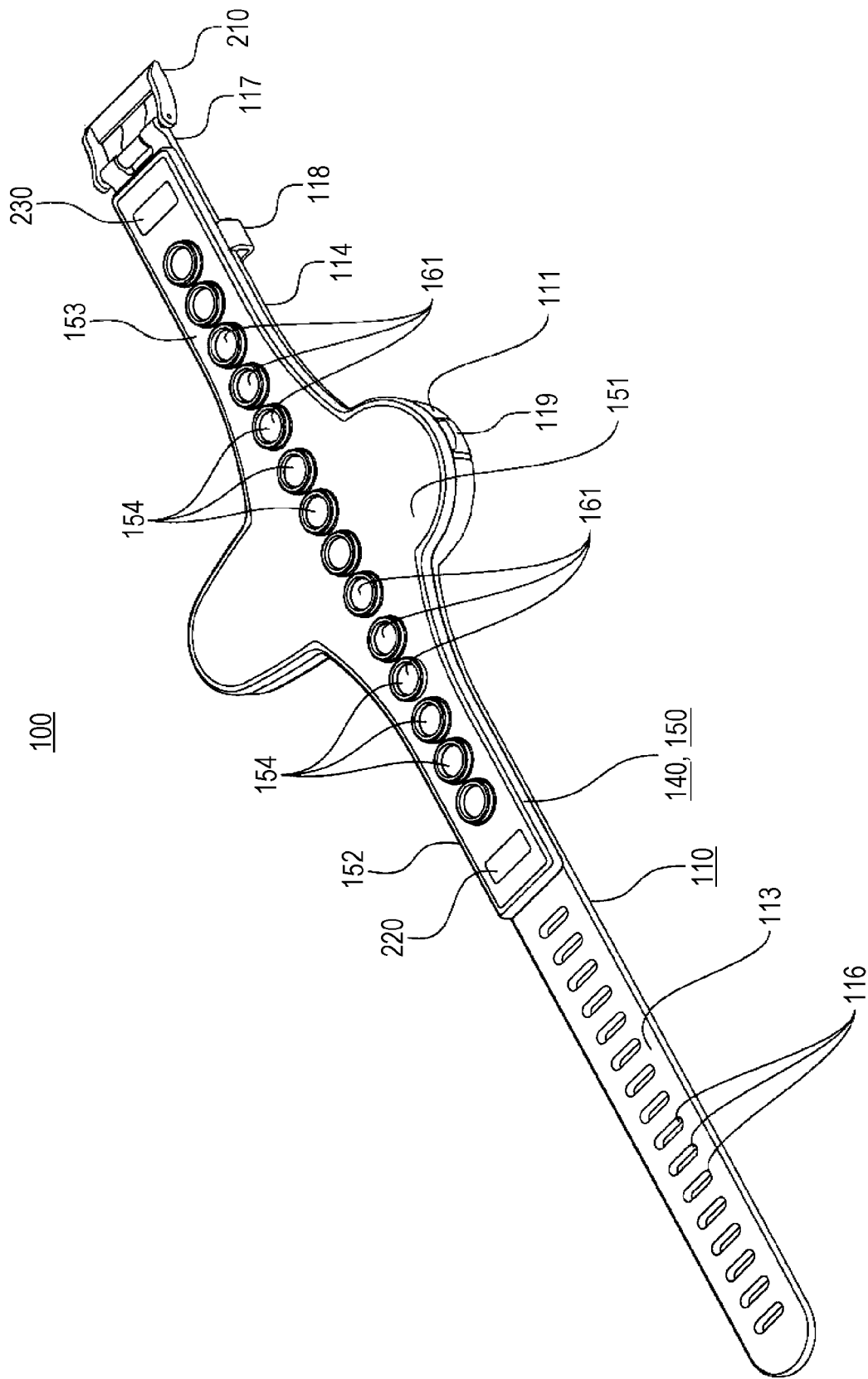
FIG. 2 is a perspective view of a rear surface side of the biological information measuring instrument according to the embodiment of the present invention.
Figure 3:
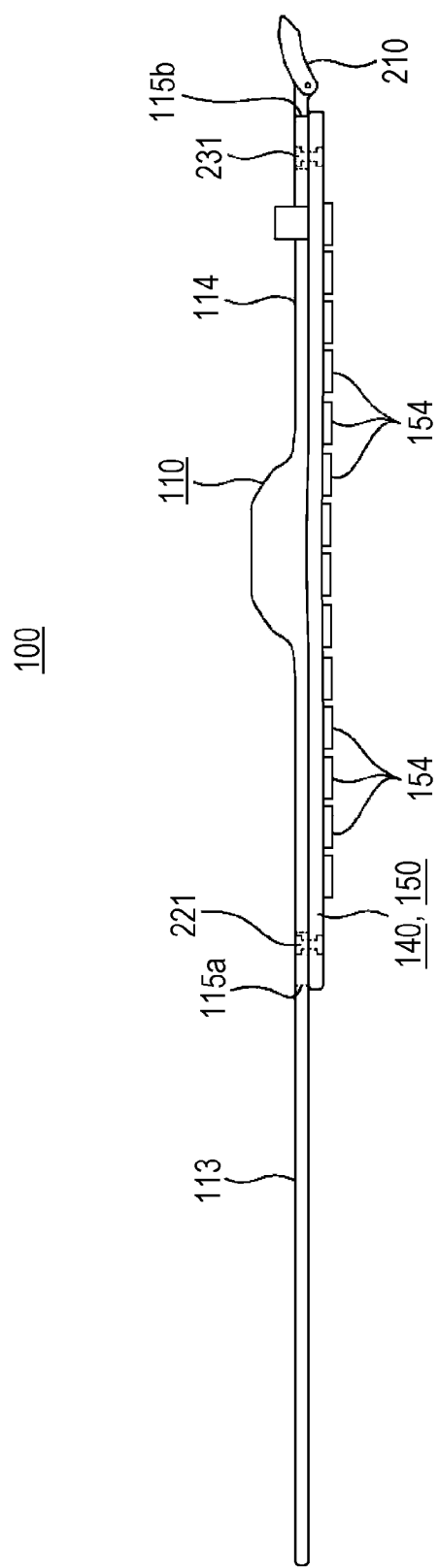
FIG. 3 is a side view of the biological information measuring instrument according to the embodiment of the present invention.
Figure 4:
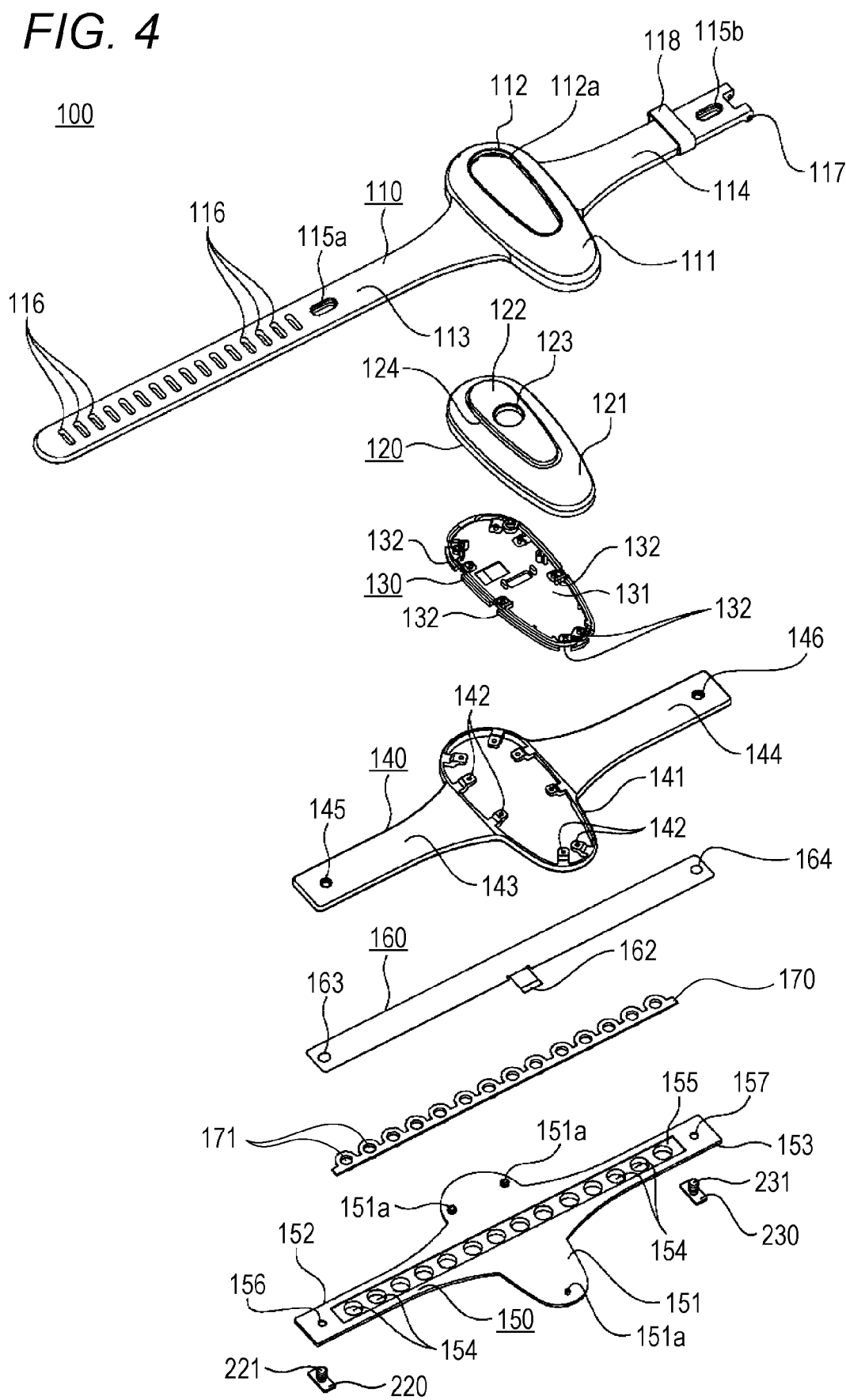
FIG. 4 is an exploded perspective view of the front surface side of the biological information measuring instrument according to the embodiment of the present invention.
Figure 5:
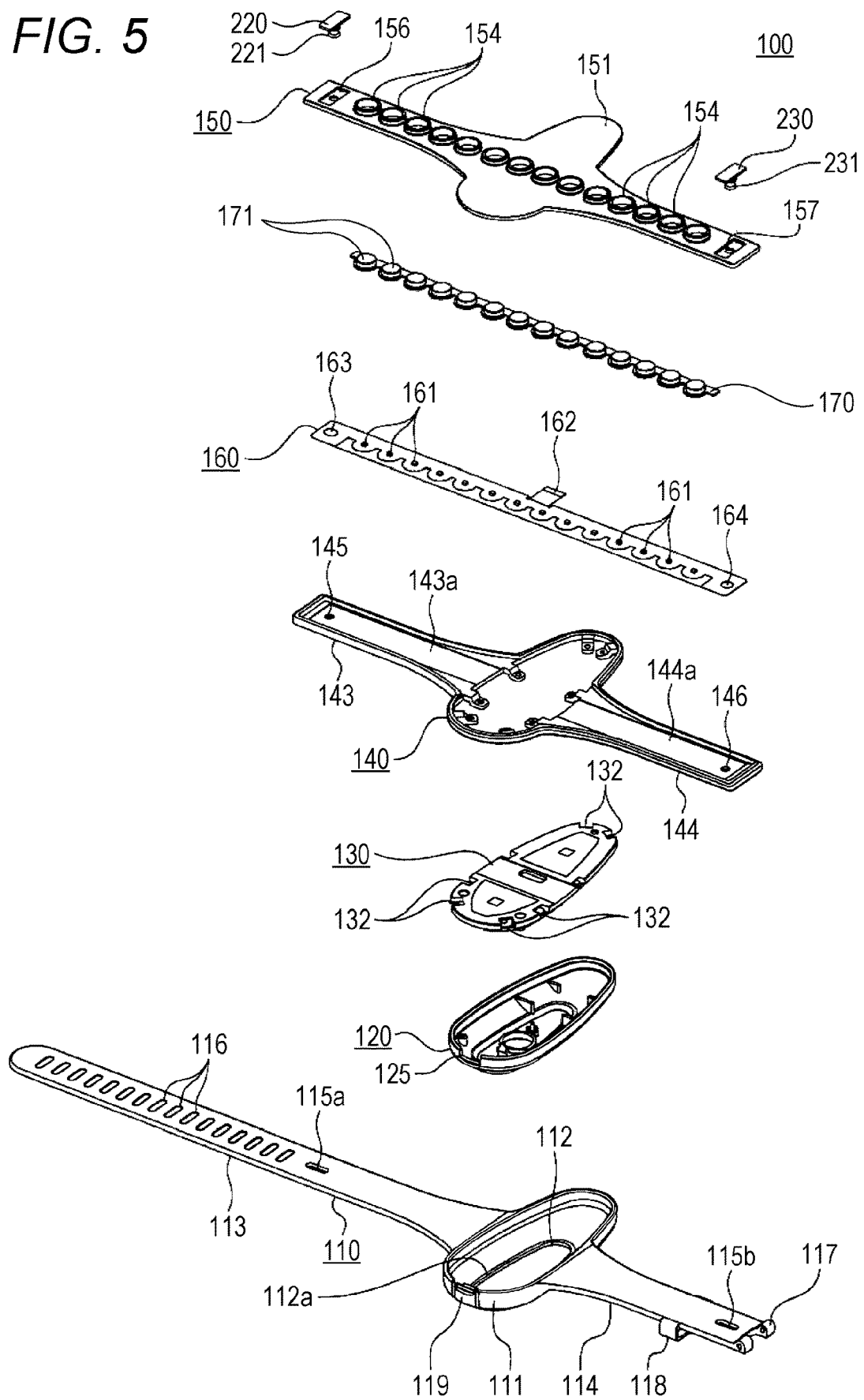
FIG. 5 is an exploded perspective view of the rear surface side of the biological information measuring instrument according to the embodiment of the present invention.

FIGS. 1 and 2 respectively show a front surface side and a rear surface side of a biological information measuring instrument 100 of the present embodiment, and FIG. 3 shows a side surface of the biological information measuring instrument 100. Further, FIGS. 4 and 5 are exploded perspective views showing components constituting the biological information measuring instrument 100 of the present embodiment in an exploded manner, FIG. 4 is the exploded perspective view seen from the front surface side, and FIG. 5 is the exploded perspective view seen from the rear surface side. However, in the exploded perspective views of FIGS. 4 and 5, some components arranged inside a circuit board, a battery, and the like are omitted.

Figure 6:
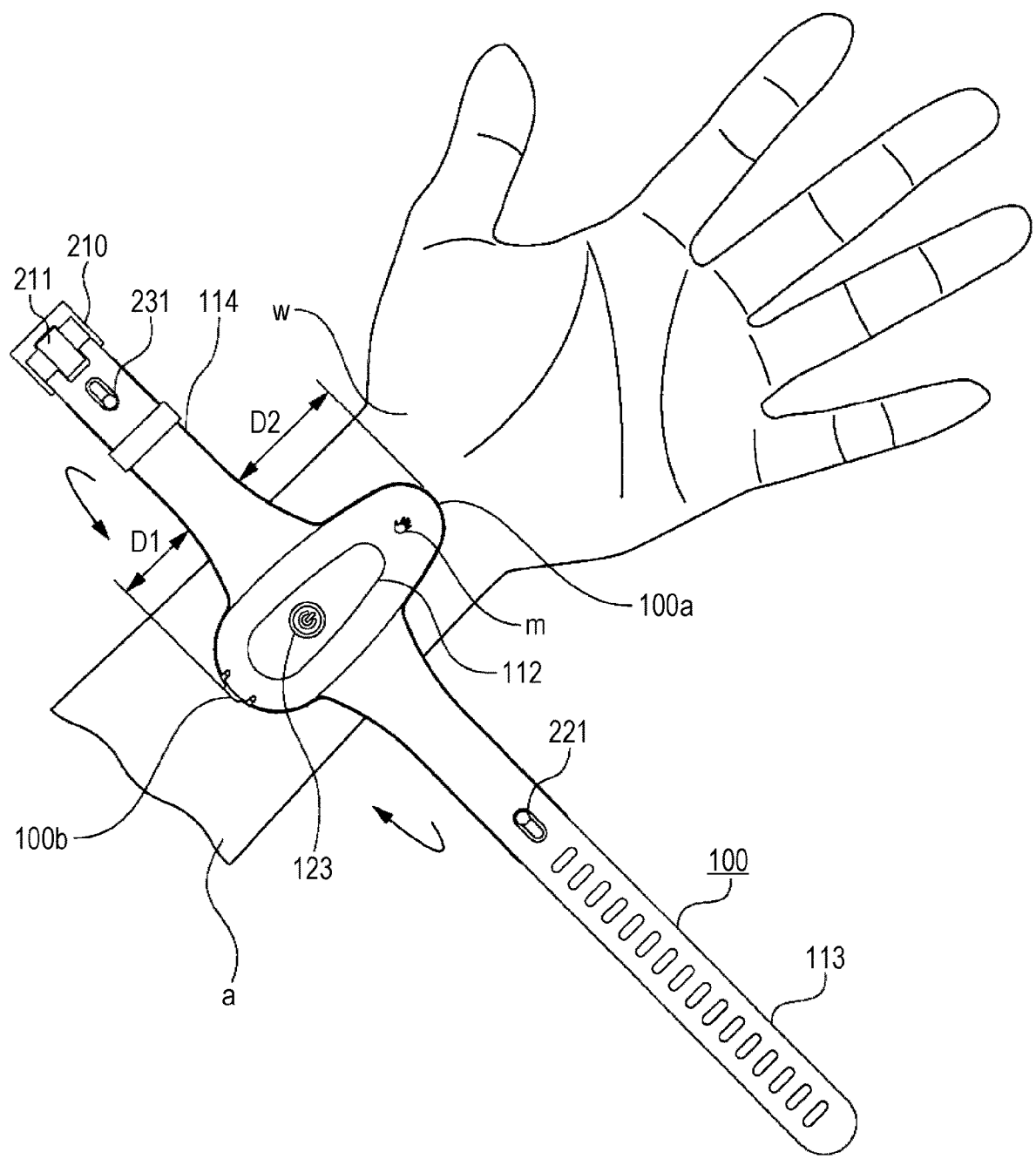
FIG. 6 is a perspective view showing a state immediately before the biological information measuring instrument is worn according to the embodiment of the present invention.
Figure 7:
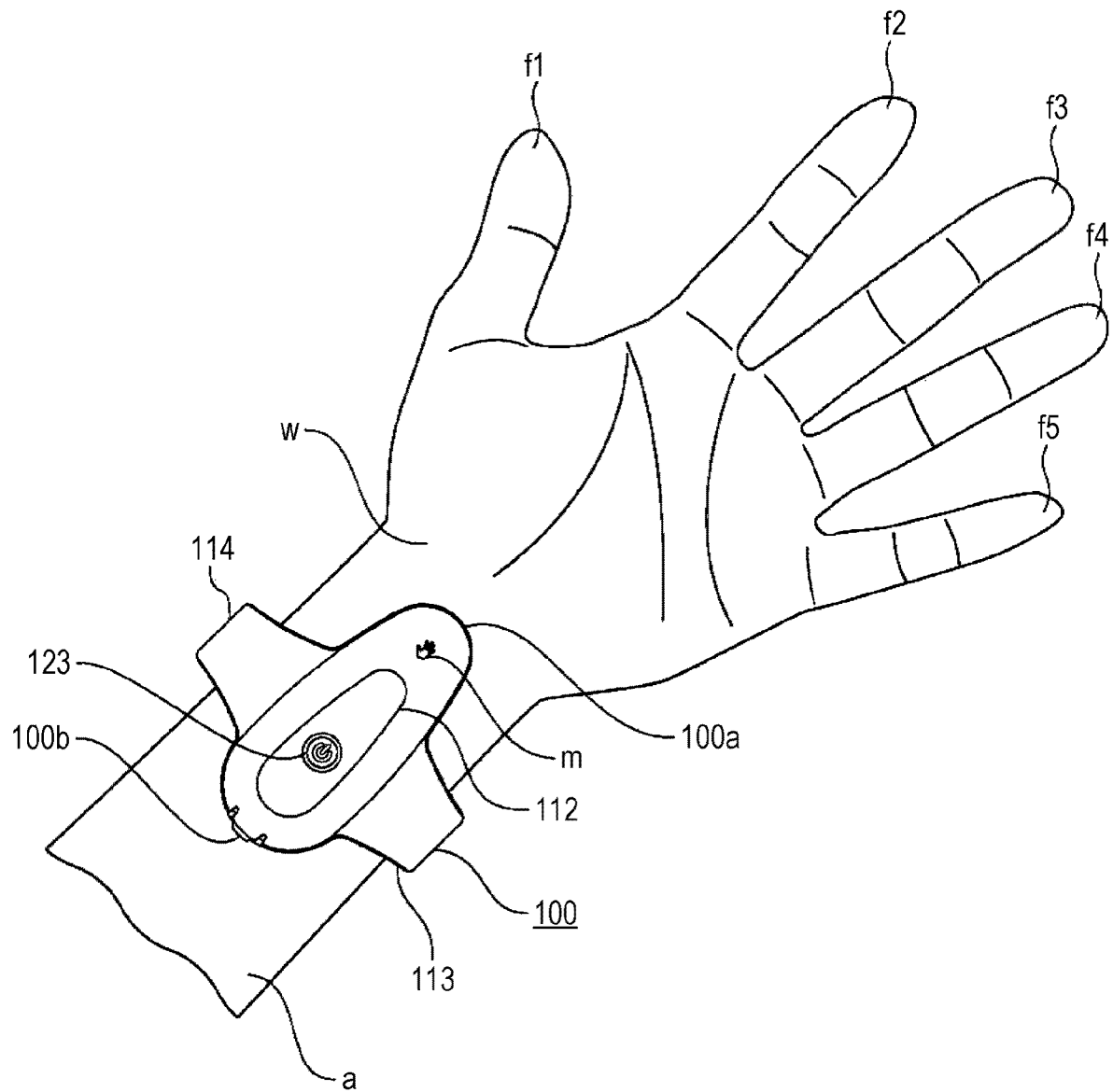
FIG. 7 is a perspective view showing a wearing state of the biological information measuring instrument according to the embodiment of the present invention.

The biological information measuring instrument 100 of the present embodiment is to be worn around a user's arm as shown in FIGS. 6 and 7 described below. The biological information measuring instrument 100 worn on the arm is used as a controller that measures movement of a wrist w or fingers f1 to f5 from a displacement of an arm muscle and performs an operation such as a game based on a measurement result. Note that use of the biological information measuring instrument 100 of the present embodiment as the controller for the game is merely an example, and the biological information measuring instrument 100 of the present embodiment can be used as the controller for controlling various electronic devices such as robots and computers, and software.

First, an overall structure of the biological information measuring instrument 100 will be described.

The biological information measuring instrument 100 includes a first belt member 110 which is a member to be wound around the arm. The first belt member 110 includes a cover 111 that covers a part of a front surface portion 121 of a case lid 120, and a sword tip-side belt 113 and a parent-side belt 114 connected to the cover 111. The first belt member 110 is formed of a flexible resin such as silicone rubber.

The case lid 120 is a member that forms a case body by being joined to a case bottom surface 130 shown in FIGS. 4 and 5. Although not shown in the exploded perspective views of FIGS. 4 and 5, the circuit board mounted with circuit components for performing a measurement process and the like as the biological information measuring instrument 100, and a battery are built in the case body. The case lid 120 and the case bottom surface 130 are formed of a relatively hard resin such as an ABS resin (acrylonitrile butadiene styrene resin).

Second belt members 140 and 150 are arranged on the rear surface side of the case bottom surface 130. The second belt members 140 and 150 are formed by integrally joining the second belt member 140 on the front surface side and the second belt member 150 on the rear surface side by bonding or the like. The second belt member 140 on the front surface side and the second belt member 150 on the rear surface side are formed of the flexible resin such as silicone rubber.

Further, as shown in FIGS. 4 and 5, a sensor substrate 160 is built in between the second belt member 140 on the front surface side and the second belt member 150 on the rear surface side. In the following description, the second belt member 140 on the front surface side is referred to as the second belt member (front side), and the second belt member 150 on the rear surface side is referred to as the second belt member (rear side).

Next, a detailed structure of each component will be described.

A plurality of wearing holes 116 are arranged at predetermined intervals in the sword tip-side belt 113 connected to the cover 111 of the first belt member 110. Further, a buckle connection portion 117 is formed at a tip of the parent-side belt 114, and a buckle 210, which is a mechanical component for connecting with the sword tip-side belt 113, is attached thereto. When the biological information measuring instrument 100 is worn on the arm, a tip of the sword tip-side belt 113 is passed through the buckle 210 and a fixing rod 211 attached to the buckle 210 is fitted into one of the wearing holes 116 in the sword tip-side belt 113. The biological information measuring instrument 100 can cope with a difference in size of the user's arm by selecting one of the wearing holes 116 into which the fixing rod 211 is fitted.

In addition, elongated holes 115a and 115b for connecting with the second belt members 140 and 150 are formed in the sword tip-side belt 113 and the parent-side belt 114 of the first belt member 110. Further, a ring 118 for passing the sword tip-side belt 113 is disposed near the buckle connection portion 117 of the parent-side belt 114 of the first belt member 110.

As shown in FIG. 4, the cover 111 in a center of the first belt member 110 has a shape that covers the front surface portion 121 of the case lid 120, and a through-hole 112 is formed substantially in a central portion of the cover 111. A wall 112a is formed at an edge of the through-hole 112.

Then, when the cover 111 is put on the front surface portion 121 of the case lid 120, an upper surface portion 122 of the case lid 120 is exposed through the through-hole 112. A button 123 that functions as a power switch is disposed on the upper surface portion 122 of the case lid 120.

Note that a groove 124 is formed around the upper surface portion 122 of the case lid 120, and when the cover 111 is put on the case lid 120, the wall 112a on the cover 111 side is fitted into the groove 124 on the case lid 120 side. Further, as shown in FIG. 5, a terminal lid 119 is formed integrally with an end of the cover 111 of the first belt member 110. The terminal lid 119 is a member that covers a terminal (not shown) disposed in the case body.

Further, as shown in FIG. 1, a mark m imitating a shape of a hand is formed on a surface of the cover 111 in the center of the first belt member 110 by engraving, printing, or the like. The mark m functions as a guide for a wearing direction when the biological information measuring instrument 100 is worn on the arm.

A component placement location 131 is formed on the case bottom surface 130 joined to the case lid 120, and the circuit board and the battery (not shown) are attached to the component placement location 131.

Note that as shown in FIG. 1, the case body covered by the cover 111 has a shape protruding from a lateral width of the sword tip-side belt 113 and the parent-side belt 114, and protrusion amounts D1 and D2 (see FIGS. 1 and 6) from the lateral width of the belts 113 and 114 are different between one protrusion amount D1 and the other protrusion amount D2. When the biological information measuring instrument 100 is worn near the wrist of the arm, the case body protrudes by the protrusion amounts D1 and D2 in the longitudinal direction of the arm, which is a direction perpendicular to the sword tip-side belt 113 and the parent-side belt 114. Here, in the present embodiment, a side closer to the wrist of the arm has the long protrusion amount D2, and an opposite side (closer to an elbow) has the short protrusion amount D1.

Notches 132 are formed in a plurality of locations around the case bottom surface 130, and connecting pieces 142 formed in a frame 141 in a center of the second belt member (front side) 140 are inserted into the notches 132. The connecting pieces 142 of the second belt member (front side) 140 are inserted into the notches 132 of the case bottom surface 130, so that the second belt member (front side) 140 is connected to the case bottom surface 130.

As shown in FIG. 4, the second belt member (front side) 140 has a sword tip-side belt 143 and a parent-side belt 144 attached to the frame 141 in the center thereof. Further, as shown in FIG. 5, concave portions 143a and 144a are respectively formed on an inner side (a rear side) of the sword tip-side belt 143 and the parent-side belt 144 for disposing the sensor substrate 160.

As shown in FIG. 5, the second belt member (rear side) 150 has a plurality of tubular portions 154 continuously arranged on an outer side (a rear side) of a sword tip-side belt 152 and a parent-side belt 153. As shown in FIG. 4, lens portions 171 of an optical lens array 170 are respectively fitted into the tubular portions 154.

Further, as shown in FIG. 4, the second belt member (rear side) 150 includes a sensor substrate placement portion 155. Then, the second belt member (front side) 140 and the second belt member (rear side) 150 are joined with the sensor substrate 160 interposed therebetween.

As shown in FIG. 5, a plurality of sensors 161 are continuously arranged on the sensor substrate 160. The lens portions 171 fitted into the tubular portions 154 of the second belt member (rear side) 150 are respectively arranged in proximity to the sensors 161, and the displacement of the arm muscle wound around with the biological information measuring instrument 100 is detected by the sensor 161.

As the sensor 161, for example, an optical distance sensor that detects a distance using infrared rays is used. The sensor substrate 160 has a connection portion 162 substantially at a center thereof, and is connected to a circuit board (not shown) disposed on the case bottom surface 130. Then, a process of detecting the displacement of the muscle is performed by an integrated circuit (not shown) attached to the circuit board. Information on the detected displacement of the muscle is wirelessly transmitted to an external instrument by a wireless communication circuit attached to the circuit board.

Note that holes 163 and 164 are formed at one end and the other end of the sensor substrate 160.

Further, as shown in FIG. 4, the second belt member (rear side) 150 includes a plurality of screw holes 151a in a central portion 151. The central portion 151 of the second belt members 140 and 150 is fixed to the case lid 120 and the case bottom surface 130 by screws (not shown) inserted into the plurality of screw holes 151a.

Then, a hole 145 is formed at the tip of the sword tip-side belt 143 of the second belt member (front side) 140, and a hole 146 is formed at the tip of the parent-side belt 144 of the second belt member (front side) 140. Further, a hole 156 is formed at the tip of the sword tip-side belt 152 of the second belt member (rear side) 150, and a hole 157 is formed at the tip of the parent-side belt 153 of the second belt member (rear side) 150.

The holes 145, 146, 156, 157 of the second belt members 140, 150 are used to connect the second belt members 140, 150 to the first belt member 110 using connection fittings 220, 230. That is, as shown in FIGS. 4 and 5, the connection fittings 220 and 230 are attached to the holes 156 and 157 of the second belt member (rear side) 150. The connection fittings 220 and 230 respectively have pins 221 and 231 as shown in FIG. 4. Each of the pins 221 and 231 has a slightly bulged tip.

When assembled as the biological information measuring instrument 100, the pins 221 and 231 are fitted into the elongated holes 115a and 115b of the first belt member 110 through the holes 163 and 164 of the sensor substrate 160 and the holes 145 and 146 of the second belt member (front side) 140. Here, bulged portions of tips of the pins 221 and 231 are formed slightly wider than lateral widths of the elongated holes 115a and 115b. Thus, as shown in FIG. 1, a state in which the pins 221 and 231 are fitted into the elongated holes 115a and 115b is maintained. Further, the pins 221 and 231 can slide along the elongated holes 115a and 115b of the first belt member 110. The pins 221 and 231 are slid when absorbing displacement between positions of the first belt member 110 and the second belt members 140 and 150 when the biological information measuring instrument 100 is worn around the arm. Details of operation of absorbing the displacement will be described below.

2. Wearing State of Biological Information Measuring Instrument

Next, a wearing state when the biological information measuring instrument 10 of the present embodiment is worn on the arm will be described with reference to FIGS. 6 to 8.

First, the user who is going to wear the biological information measuring instrument 10 places the biological information measuring instrument 10 on an arm a near the wrist w as shown in FIG. 6, and bends the sword tip-side belt 113 and the parent-side belt 114 of the first belt member 110, to wind the belts on the arm. Here, by fitting the fixing rod 211 of the buckle 210 into the wearing hole 116 of the sword tip-side belt 113 of the first belt member 110, a state of being worn on the arm a is maintained.

When placing the biological information measuring instrument 10 on the arm a, the wearing direction is determined by the mark m imitating the shape of the hand on the surface of the cover 111. That is, the user wears the biological information measuring instrument 10 in a state in which a portion of the cover 111 disposed with the mark m imitating the shape of the hand is near the wrist w.

Here, the case body of the biological information measuring instrument 10 has a shape protruding from the lateral width of the sword tip-side belt 113 and the parent-side belt 114 by the protrusion amounts D1 and D2 as described above. In particular, by making the protrusion amount D2 on the side closer to the wrist w larger than the protrusion amount D1 on the opposite side, the biological information measuring instrument 10 is worn on the arm a away from the wrist w by at least the large protrusion amount D2 when the user wears it. That is, when trying to wear the biological information measuring instrument 10 on a position closer to the wrist w than positions shown in FIGS. 6 and 7, the case body overlaps the wrist w, and the wrist w is in contact with the case body when the wrist w is bent, which results in an undesired wearing state. Therefore, the user can automatically wear the biological information measuring instrument 10 at a distance of the protrusion amount D2 in order to avoid such contact with the wrist w.

As shown in FIG. 7, by wearing the case body of the biological information measuring instrument 10 on the arm a away from the wrist w by the protrusion amount D2, the sensor 161 disposed on the biological information measuring instrument 10 can detect the displacement of the muscle at an appropriate position. That is, it is preferred that the sensor 161 disposed on the biological information measuring instrument 10 detect the displacement of the muscle of the arm a at a position at least a few centimeters inside (shoulder side) from the wrist w. With an appropriate setting of the protrusion amount D2 described above, the displacement of the muscle of the arm a can be appropriately detected automatically. That is, by setting the protrusion amount D2 to be substantially equal to a distance between the position of the arm suitable for the sensor 161 to detect the displacement of the muscle and the position of the wrist, the user can automatically wear the biological information measuring instrument 10 at a position in which it can properly detect the displacement of the muscle.

Figure 8:
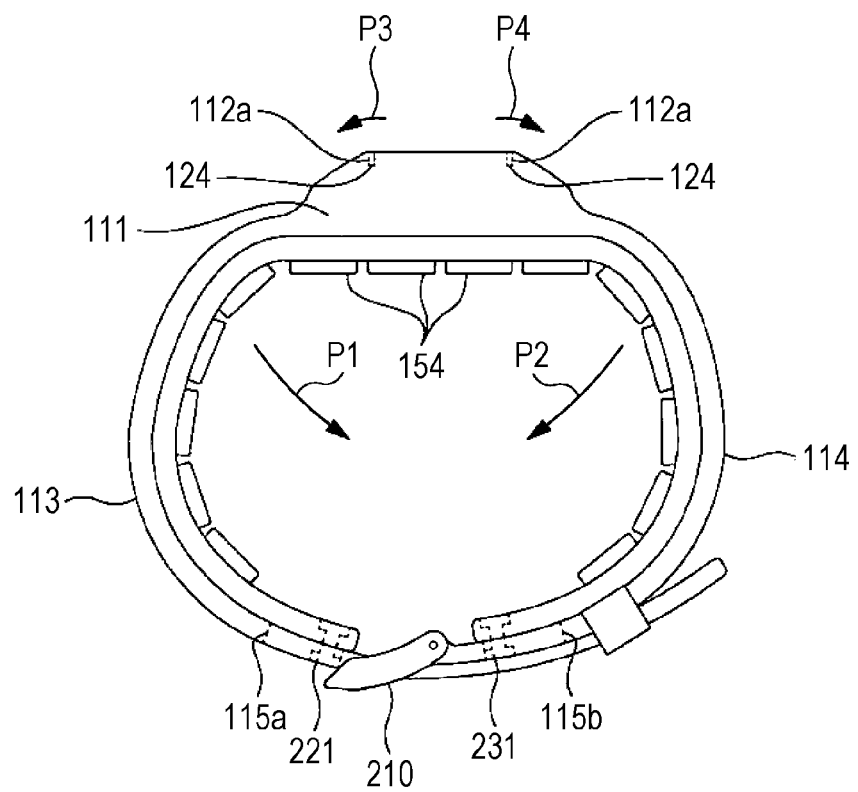
FIG. 8 is a plan view showing the wearing state of the biological information measuring instrument according to the embodiment of the present invention.

FIG. 8 shows a state in which the sword tip-side belt 113 of the first belt member 110 of the biological information measuring instrument 10 is connected to the parent-side belt 114.

As shown in FIG. 8, in a state in which the biological information measuring instrument 10 is worn on the arm, tips of the tubular portions 154 formed inside the second belt members 140 and 150 are in contact with a surface of the arm, and the sensors 161 (FIG. 5) arranged inside the second belt members 140 and 150 detect displacement of the arm muscle. Here, in the present embodiment, since the lens portions 171 (FIG. 5) are respectively fitted into the tubular portions 154, detection of the displacement of the muscle by the sensor 161 can be performed with high accuracy.

Further, since the first belt member 110 and the second belt members 140 and 150 are fixed at a central portion thereof by screwing using the screw holes 151a (FIG. 4), and ends thereof are connected slidable to some extent using the connection fittings 220 and 230, the displacement between the positions of the first belt member 110 and the second belt members 140 and 150 at the time of wearing can be absorbed.

That is, as shown in FIG. 1, when the first belt member 110 and the second belt members 140 and 150 are linearly extended, the pin 221 and 231 connecting the first belt member 110 and the second belt members 140 and 150 are located on an inner side (closer to the center) of the elongated holes 115a and 115b. Then, in a state in which the belt members are wound around the arm as shown in FIG. 8, the pins 221 and 231 are located on an outer side of the elongated holes 115a and 115b due to a difference between radii of the first belt member 110 and the second belt members 140 and 150 when they are bent.

As described above, positions of the pins 221 and 231 slide along the elongated holes 115a and 115b at the time of wearing, so that the displacement between the positions of the first belt member 110 and the second belt members 140 and 150 at the time of wearing is well absorbed. By being able to appropriately absorb this displacement, the tip of the cylindrical portion 154 of the second belt members 140 and 150 comes into close contact with the arm when worn on the arm, so that the displacement of the muscle of the arm can be favorably detected.

Note that as shown in FIG. 8, when the first belt member 110 and the second belt members 140 and 150 are bent and worn on the arm, forces P1 and P2 for inwardly bending the belt members 110, 140 and 150 act, so that forces P3 and P4 that pull the center cover 111 in the longitudinal direction of the first belt member 110 are generated. When the forces P3 and P4 are generated, there is a possibility that the edge of the through-hole 112 of the cover 111 is directly pulled and the cover 111 comes off from the case lid 120. However, in the present embodiment, since the wall 112a formed at the edge of the through-hole 112 of the cover 111 is fitted into the groove 124 of the case lid 120, the cover 111 does not come off.

As described above, since the case body has a shape protruding from the belt members 110, 140, and 150, the biological information measuring instrument 10 of the present embodiment is automatically worn on a position away from the wrist by a certain distance, which is an appropriate position for the sensor to detect the displacement of the muscle in conjunction with the movement of the finger or the wrist when it is worn on the arm. Therefore, the movement of the finger or wrist of the user wearing the biological information measuring instrument 10 of the present embodiment can be measured well. Moreover, since the biological information measuring instrument 10 of the present embodiment is a very simple mechanism that can be simply wound around the arm with the belt members 110, 140 and 150, and is small in size, it does not give the user a sense of discomfort wearing a foreign object.

Then, by separating the belt member into the second belt members 140 and 150 incorporating the sensor substrate 160 therein and the first belt member 110 in which the mechanical component to be wound around the arm is attached on the front surface side, a state of use as the biological information measuring instrument 10 can be improved. That is, the first belt member 110 attached with the mechanical component wound around the arm may be worn out and damaged by repeated wearing on the arm, but can be relatively easily removed and replaced. On the other hand, the second belt members 140 and 150 incorporating the sensor substrate 160 and the like therein have no members that are worn out when worn on the arm, and can increase durability as the measuring instrument.

3. Modifications

Note that a shape of each component of the biological information measuring instrument 100 shown in FIGS. 1 to 8 is a preferred example, and is not limited to the illustrated shape. For example, shapes of the case lid 120 and the case bottom surface 130 shown in FIGS. 1 and 4 are merely examples, and the case body may have another external shape.

Further, as shown in an exploded manner in FIG. 4 and the like, the case body is formed separately from the belt member, but the belt member and the case body may be integrated.

Note that in the present embodiment, the belt member is divided into the first belt member 110 and the second belt members 140 and 150, but may be integrally formed. As for a mechanism for wearing the biological information measuring instrument 100 on the arm, the buckle 210 widely used as a so-called wristwatch belt is used, but it may be worn on the arm using another mechanism.

Further, although the second belt members 140 and 150 have a shape in which the second belt member (front side) 140 and the second belt member (rear side) 150 are bonded, they may be integrally formed.

LIST OF REFERENCE NUMERALS

100 Biological information measuring instrument
100a, 100b Protruding end
110 First belt member
111 Cover
112 Through-hole
112a Wall
113 Sword tip-side belt
114 Parent-side belt
115a, 115b Elongated hole
116 Wearing hole
117 Buckle connection portion
118 Ring
119 Terminal lid
120 Case lid
121 Front surface portion
122 Upper surface portion
123 Button
124 Groove
130 Case bottom surface
131 Component placement location
132 Notch
140 Second belt member (front side)
141 Frame
142 Connecting piece
143 Sword tip-side belt
144 Parent-side belt
145, 146 Hole
150 Second belt member (rear side)
151 Central portion
151a Screw hole
152 Sword tip-side belt
153 Parent-side belt
154 Tubular portion
155 Sensor substrate placement portion
156, 157 Hole
160 Sensor substrate
161 Sensor
162 Connection portion
163, 164 Hole
170 Optical lens array
171 Lens portion
210 Buckle
211 Fixing rod
220, 230 Connection fitting
221, 231 Pin
a Arm
w Wrist
f1 to f5 Finger

The invention claimed is:

1. A biological information measuring instrument comprising:
   a belt portion that is worn on a user's arm in a circumferential direction of the arm and disposed with a sensor for detecting a displacement of an arm muscle; and
   a case portion that is attached to a predetermined portion of the belt portion and houses a circuit component that processes a signal of the displacement detected by the sensor, wherein
   the case portion has a shape of protruding from the belt portion in a longitudinal direction of the arm when the belt portion is worn on the arm, and amounts of protrusions protruding in the longitudinal direction are different between one protrusion and the other protrusion,
   the belt portion comprises:
   a first belt member attached with a mechanical component for connecting one end and the other end of the belt portion when the belt portion is worn on the arm; and
   a second belt member that is disposed on a rear surface side of the first belt member, disposed with the sensor, and in contact with the arm when the belt portion is worn on the arm, and
   the first belt member and the second belt member are connected to be slidable in the circumferential direction of the arm.

2. The biological information measuring instrument according to claim 1, wherein
   the first belt member is integrally formed with a cover that covers a part of a surface of the case portion, and
   a part of the cover is provided with a wall fitted into a groove formed on the surface of the case portion.

3. The biological information measuring instrument according to claim 1, wherein
   an optical lens is disposed at a position in which the sensor is attached to the belt portion.

4. The biological information measuring instrument according to claim 1, wherein
   the amount of one protrusion of the case portion from the belt portion is substantially equal to a distance between an arm position suitable for the sensor to detect the displacement of the muscle and a wrist position.

* * * * *